United States Patent
Valerino, Sr.

(10) Patent No.: US 9,630,787 B2
(45) Date of Patent: Apr. 25, 2017

(54) PNEUMATIC TUBE CARRIER ROUTING AND TRACKING SYSTEM

(71) Applicant: Fredrick M. Valerino, Sr., Timonium, MD (US)

(72) Inventor: Fredrick M. Valerino, Sr., Timonium, MD (US)

( * ) Notice: Subject to any disclaimer, the term of this patent is extended or adjusted under 35 U.S.C. 154(b) by 0 days.

(21) Appl. No.: 14/483,655

(22) Filed: Sep. 11, 2014

(65) Prior Publication Data

US 2015/0025675 A1  Jan. 22, 2015

(51) Int. Cl.
| | |
|---|---|
| G06F 7/00 | (2006.01) |
| B65G 51/42 | (2006.01) |
| G06Q 10/08 | (2012.01) |
| G06Q 10/00 | (2012.01) |
| G06Q 50/10 | (2012.01) |
| G06Q 50/30 | (2012.01) |
| B65G 51/04 | (2006.01) |
| B65G 51/44 | (2006.01) |
| B65G 51/46 | (2006.01) |
| G06F 19/00 | (2011.01) |

(52) U.S. Cl.
CPC ............ *B65G 51/42* (2013.01); *B65G 51/04* (2013.01); *B65G 51/44* (2013.01); *B65G 51/46* (2013.01); *G06F 19/70* (2013.01); *G06Q 10/00* (2013.01); *G06Q 10/08* (2013.01); *G06Q 50/10* (2013.01); *G06Q 50/30* (2013.01)

(58) Field of Classification Search
USPC .......................................................... 700/229
See application file for complete search history.

(56) References Cited

U.S. PATENT DOCUMENTS

| | | | | |
|---|---|---|---|---|
| 6,146,057 A | * | 11/2000 | Gromley ................ | B65G 51/26 406/10 |
| 6,561,691 B1 | * | 5/2003 | McCann .................. | F25C 5/007 366/299 |
| 7,243,002 B1 | * | 7/2007 | Hoganson .............. | B65G 51/44 406/4 |

* cited by examiner

*Primary Examiner* — Kyle Logan
(74) *Attorney, Agent, or Firm* — Kelley Drye & Warren LLP

(57) ABSTRACT

A system and method provides for a pneumatic tube carrier routing and tracking system having a system control module that captures and presents tracking information associated with sending and receiving carriers. The pneumatic tube carrier tracking system comprises sending and receiving stations connected by pneumatic tubing, and which are configured to securely send carriers, with receiving users optionally being restricted from unauthorized access of carriers. The receiving station further comprises a plurality of receiving bins, each comprising a door for preventing access to the receiving bin by unauthorized users. The sending and receiving stations have identifying tag readers configured to scan identifier tags to read carrier delivery, carrier receipt and receiving user information. Destination and intended recipient information are entered at the sending station when sending a carrier and are transmitted to a system control module, which routably delivers and secures the carriers in response the destination and intended recipient information.

22 Claims, 12 Drawing Sheets

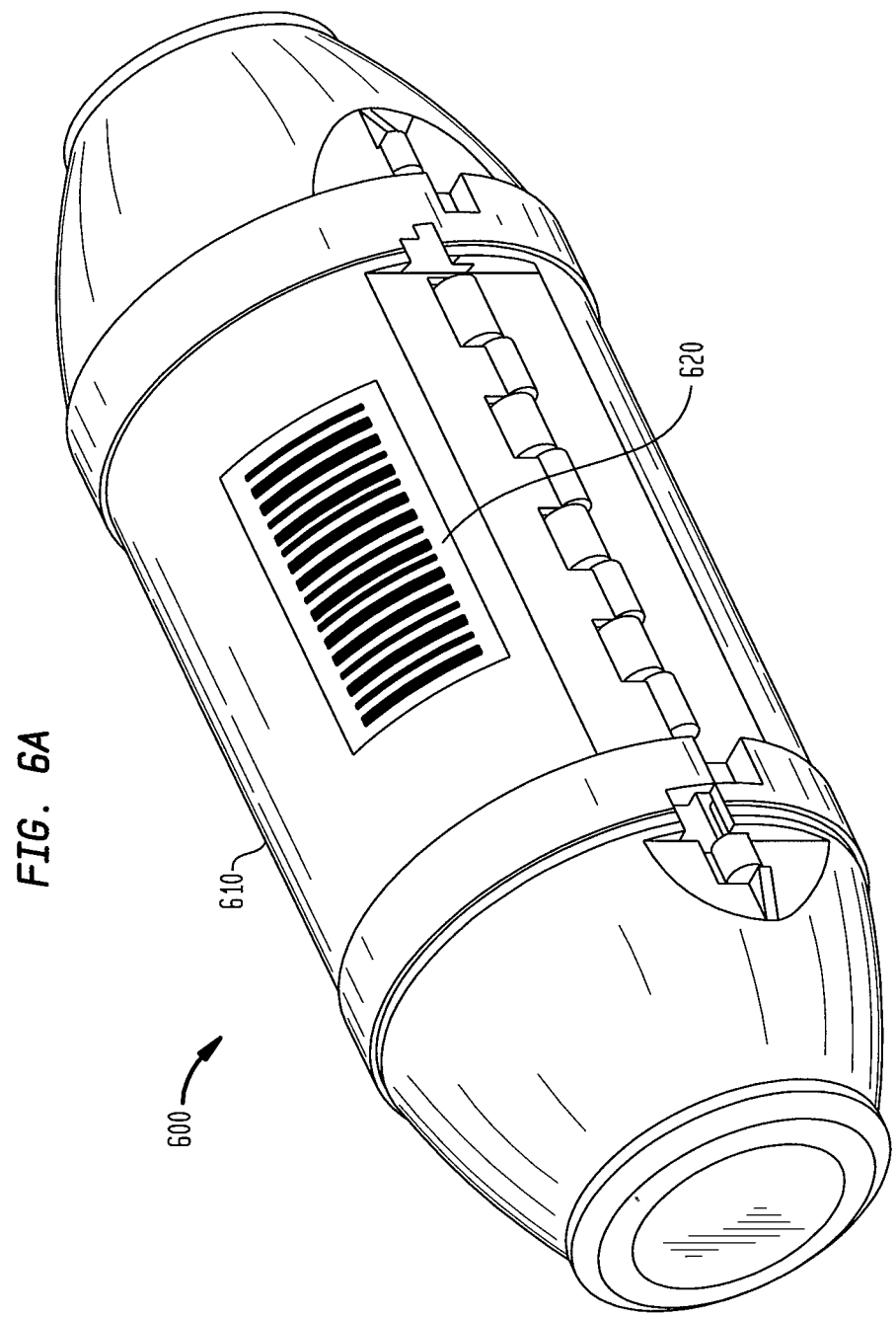

PNEUMATIC TUBE CARRIER ROUTING AND TRACKING SYSTEM

FIELD OF THE INVENTION

The present principles generally relate to pneumatic tube delivery systems. More specifically, the present principles refer to a system and method for routing and tracking carriers and associated payloads in pneumatic tube delivery systems directly to an end user.

BACKGROUND OF THE INVENTION

In large institutional settings such as hospitals, the dispensing and delivery of drugs has become a time consuming process. In particular, sterile items, controlled medications, biological samples, and the like need to be prepared and transported in a secure environment while ensuring the safety of patients and hospital workers.

Transporting objects via pneumatic tubes is known to the art. Pneumatic delivery systems are used extensively for the rapid and efficient transportation of a wide variety of articles. These delivery systems are used in a number of business operations, including, but not limited to, banks, hospitals, office buildings, industrial plants, and transportation terminals.

To send a payload in a carrier, an object is placed within a carrier which is then transported within enclosed pneumatic tubing by air under either positive or negative pressure to a desired destination. The interior of the closed tube and the outer dimension of the carrier form a seal so that the carrier can be propelled between the destinations by a vacuum or positive air pressure.

One specific area of commerce which currently uses the pneumatic tube for transporting materials is the hospital or biomedical research/manufacturing industry. Pneumatic tube delivery systems have proven to be particularly useful for transporting blood samples, medicines, intravenous bags, viral samples or other biological or chemical matter within hospitals or laboratories. Some of the payloads transported may be highly addictive drugs (i.e. morphine) which need to be tightly controlled.

In a hospital environment, pneumatic tube systems are also used to transport prescriptions from a pharmacy located in the hospital facility to the patient. Such pneumatic tube systems comprise a sending station located at the pharmacy in communication with a plurality of receiving stations located throughout the hospital. Each receiving station typically includes a single receiving bin such that all carriers are delivered to the single receiving bin, regardless for which patient and room the prescription within the carrier was destined. In use, when the doctor prescribes medication, the pharmacy fills the prescription and delivers it inside a carrier to a desired receiving station via the pneumatic tube system. The user at the receiving station opens the carrier and determines to which patient at which room the user needs to deliver the prescription. User error may occur during the identification of the room and patient resulting in missdelivery of the prescription. In addition, unauthorized users may have access to the carriers at the receiving station.

Thus, there is clearly a need for a system and method providing a secure pneumatic tube carrier delivery. Also a need exists for a system and method providing routing and tracking of carriers in a pneumatic tube system to a receiving bin at a receiving station associated with an end user to ensure the secure delivery of carrier contents to proper destinations and authorized end users. Furthermore, there is a need for an auditable trail indicating the chain of custody of carrier contents from the sending station to the end user.

According to the present principles there is provided a pneumatic tube carrier system for routing and tracking carriers in a pneumatic tube system comprising a pneumatic tube system, a connecting diverter with blower, and storage piping with diverters, sending and receiving stations, a system control module, and identifying tag readers configured to read identifying tags. The identifying tag readers scan delivery information to provide secure and authorized delivery of carriers and their contents. The identifying tag readers and system control together provide an efficient and secure method and system of routing and tracking carriers and carrier contents throughout the pneumatic tube system.

SUMMARY OF THE INVENTION

Presented herein is a pneumatic tube carrier routing and tracking system having a system control module that routes carriers and captures and presents tracking information associated with sending and receiving carriers. The system control module comprises a database module and a computer control center module in signal communication with the database module.

The pneumatic tube carrier tracking system further comprises a sending station and a receiving station in signal communication with the system control module. The sending station and the receiving station are routably connected by pneumatic tubing for the delivery of carriers.

The sending station has an identifying tag reader configured to scan identifier tags to obtain delivery and identifying information for a carrier. The identifying tag reader then transmits the delivery information to the system control module. The receiving station has an identifying tag reader configured to scan identifier tags to obtain and transmit reception information for a carrier to the system control module. The identifying tag reader transmits delivery information and reception information to the computer control center module which interprets delivery information and reception information and sends commands to the pneumatic tube system to control routing of the carrier in the pneumatic tubing. The database module is configured to receive and store delivery information sent to the System Control Module from the sending station and reception information from the receiving station.

In one embodiment, the receiving station comprises a plurality of receiving bins, wherein each receiving bin comprises a door preventing access to the receiving bin. The system control module comprises a database module for storing a list of users authorized to access each of the plurality of receiving bin of the receiving station. The sending station comprises a carrier receiving bin and a tag reader for reading an identification tag of a carrier or of contents of a carrier to obtain destination information. Preferably, the destination information comprises identification of one receiving bin of the plurality of receiving bins of the receiving station. The system control module receives the identification of the one receiving bin from the sending station and routes the carrier from the sending station to the one receiving bin of the receiving station through the pneumatic tubing. To unlock the one receiving bin, the system control module receives a selection of the one receiving bin and a user identification information from the receiving station or from a mobile device. The system control module verifies whether the user identification information matches a user from the list of users authorized to access the one receiving bin. If the user is authorized to access the one receiving bin, the system control module sends a command to the receiving station to unlock the door of the one receiving bin.

In one embodiment, the system comprises a tag reader that allows a user to capture unique identifiers for individual carriers and contents, sending stations, receiving stations and sending and receiving users. A database disposed within the system also permits the user to archive and retrieve data associated with sending and receiving deliveries through the pneumatic tube system. Further, the system comprises the ability to institute security measures such as holding a carrier until a receiving user's identification (hereinafter "ID") is entered into, and verified by, the tracking system.

According to a method of using the present invention, the carrier contents are prepared for a carrier to be sent to the pneumatic tube carrier tracking system. Identifying tags are scanned using the identifying tag reader at the sending station to capture delivery information. The carrier is received in a carrier receiving bin of a sending station. The delivery information is transmitted from the identifying tag reader to the system control module and the carrier is sent through the pneumatic tubing system from the sending station. The system control module receives the incoming delivery information from the identifying tag readers at the sending station and the reception information from the receiving station and logs and stores this information in the database module. The computer control center module interprets the delivery information and sends commands to the pneumatic tube system to control the operations of the system and routably deliver the carrier. The carrier is routed through the pneumatic tube system in response to the delivery information and sensed by optical sensors in the branches of the pneumatic tubing until it reaches the receiving station. The carrier is delivered to the receiving station where identifier tags are scanned by an identifying tag reader to capture reception information. The reception information is transmitted to the system control module from the identifying tag reader and the sender at the sending station is optionally notified that the carrier has been delivered. The pneumatic tube carrier tracking system allows a carrier to be routed from any station on the pneumatic tubing system to any other station.

BRIEF DESCRIPTION OF THE DRAWINGS

A further understanding of the present principles can be obtained by reference to a preferred embodiment, along with alternative embodiments, set forth in the accompanying drawings where like reference numbers indicate like elements throughout the drawings. Although the illustrated embodiments are merely exemplary of systems for carrying out the present principles, the organization and method of operation of the principles in general, together with further objectives and advantages thereof, may be more easily understood by reference to the drawings and the following description. The drawings are not intended to limit the scope of the principles, which is set forth with particularity in the claims as appended or as subsequently amended, but merely to clarify and exemplify the principles.

For a more complete understanding of the present principles, reference is now made to the following figures:

FIG. 6A is a diagram of a carrier having a bar code identifier tag according to an embodiment of the present principles.

DETAILED DESCRIPTION OF THE INVENTION

Illustrative embodiments of the present principles are disclosed herein. However, techniques, systems and operating structures in accordance with the present principles may be embodied in a wide variety of forms and modes, some of which may be different from those in the disclosed embodiment. Consequently, the specific functional details disclosed herein are merely representative, yet in that regard, they are deemed to afford the best embodiment for purposes of disclosure and to provide a basis for the claims herein which define the scope of the present principles.

Some elements of the present principles are illustrated as modules for performing described functions. While these modules may be described in terms of software implementations, any hardware, or combination of hardware and software may be used to implement the present principles without deviating from the scope or spirit thereof.

Moreover, well known methods and procedures for both carrying out the objectives of the present principles and illustrating the preferred embodiment are incorporated herein but have not been described in detail as not to unnecessarily obscure novel aspects of the present principles.

Figure 1:
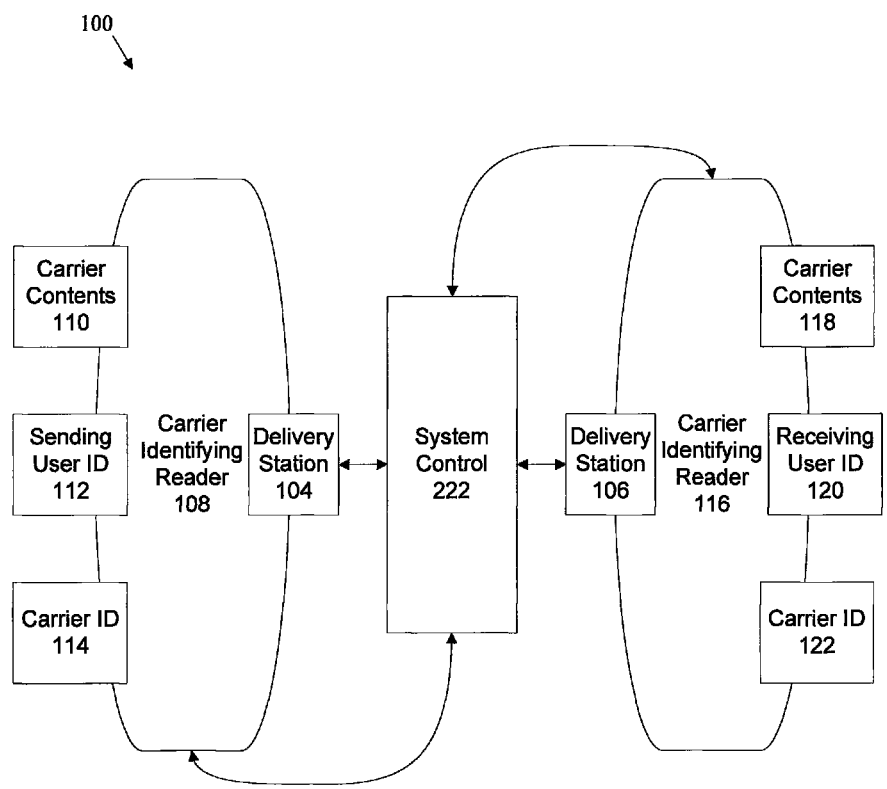
FIG. 1 is a diagram illustrating a system and method for tracking carriers and payloads in a pneumatic tube system according to an embodiment of the present principles.

Referring now to FIG. 1, a diagram illustrating a system and method for routing and tracking carriers and payloads in a pneumatic tube system 100 according to an embodiment of the present principles is shown. System control module 222 controls the operation of pneumatic tube system 100, reading, storing, and presenting data, and routing and tracking the delivery of carriers in response to the collected data. One or more identifying tag readers 108 may read and store a unique ID tag associated with the carrier contents or payload 110, or with the sending user's ID 112, the receiving user's ID 120, or the carrier ID 114. The identifying tag readers 108 may also read and store a unique ID tag associated with the sending station and delivery station. In one useful embodiment, an identifying tag reader 108 may read the ID tag of objects using an optical scanning system to read bar codes.

Alternatively, an identifying tag reader 108 may employ an optical scanning system to identify characters and read and store the ID or identifier information of various objects. In another embodiment, the identifying tag reader 108 may identify objects using RFID or other radio frequency technology. Additionally, any other identification technology known, or as yet undiscovered, may be used within the scope of the present principles. The sending user's ID may be a badge, a wristband, or the like. The identifying tag reader 108 may replace the need for a control panel, allowing all the necessary scanning, interpreting, and sending of a payload to be performed at one station. In alternative embodiments, the identifying tag reader 108 may be the sending station itself.

The identifying tag reader 108 sends identifier information from delivery station 104 to system control module 222. The delivery stations 104 and 106 may be a station primarily used to send or primarily used to receive payload containing carriers. However, delivery stations 104 and 106 may be used to both send and receive carriers.

System control module 222 receives identifier and delivery information from the identifying tag reader 108 at delivery station 104 and determines the appropriate actions to be performed on delivery station 106. For example, the system control module 222 may use the information from identifying tag reader 108 at delivery station 104 to determine to which delivery station 106 a carrier 610 will be routed and which receiving user ID 120 must be scanned in order for the receiving user to receive the carrier 610 (given that the sender requires the receiving user ID to be scanned prior to receiving the carrier). The receiving user at delivery station 106, upon receiving the carrier delivery, uses an identifying tag reader 116 to scan their ID 120, carrier contents 118, and the carrier ID 122, completing the transaction. This information is sent from the identifying tag reader 116 at delivery station 106 to system control module 222 to be recorded and stored in the system.

Figure 2:
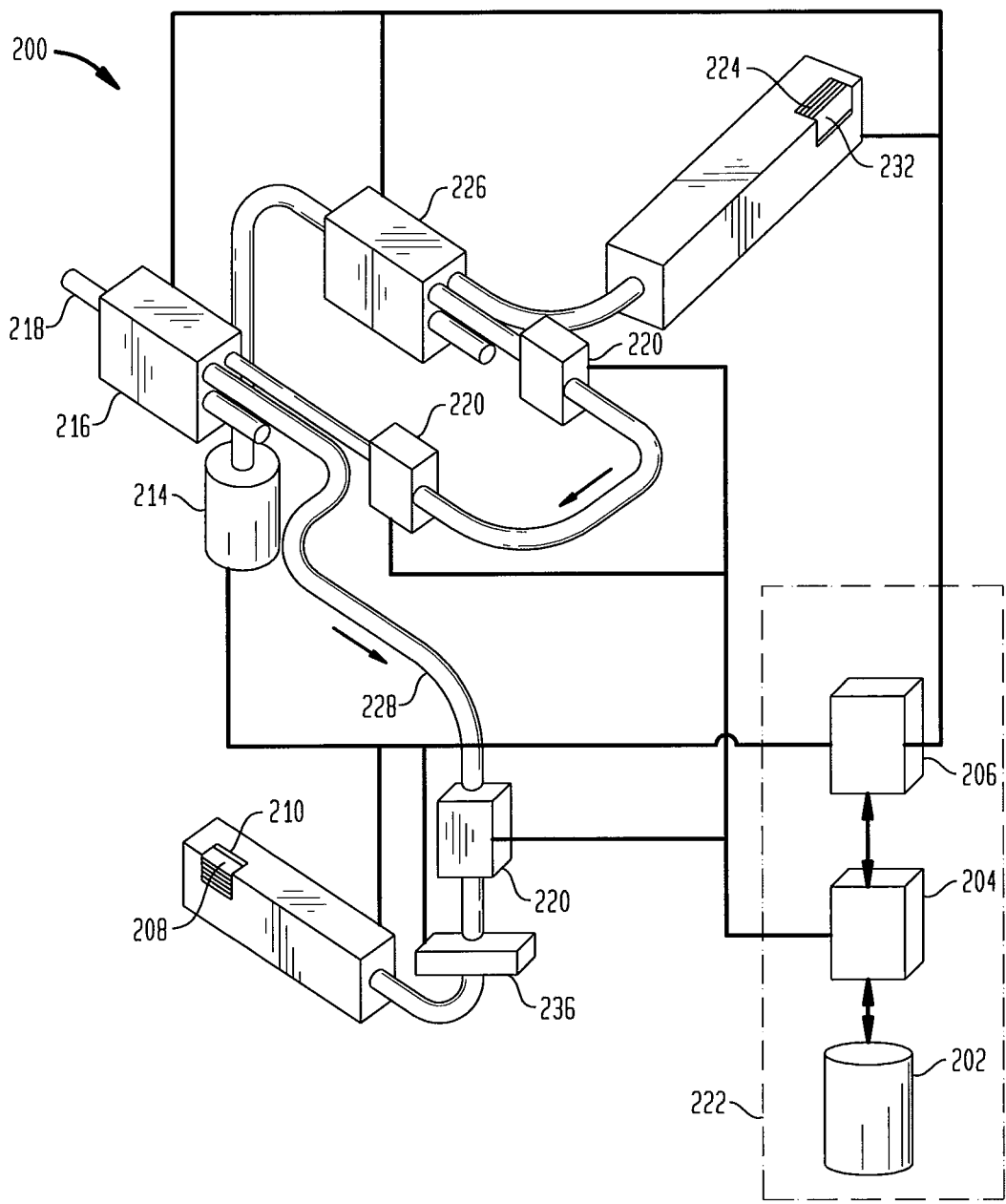
FIG. 2 is a diagram illustrating an automatic pneumatic tube system according to an embodiment of the present principles.

Referring now to FIG. 2, a diagram illustrating a pneumatic tube system 200 according to an embodiment of the present principles is shown. The pneumatic tube carrier tracking system 200 comprises transmission tubing 228, a system control module 222, and a sending station 224 and receiving station 208 for initiating the sending of carriers and receiving the sent carriers. Although FIG. 2 demonstrates a one zone pneumatic tube system 200, a system with multiple zones and the inclusion of any number of sending 224 and receiving stations 208 is possible without deviating from the scope of the present principles. The system also includes blower 214 and one or more diverters 216 and 226 which direct the transportation of carriers 610 from storage compartment 218 to sending station 224 or receiving station 208 at the direction of the system control module 222. Furthermore, pneumatic tube system 200 may include a plurality of inline identifying tag readers or optical sensors 220 configured to track or sense the carriers as they are transported through the tubing 228. The inline identifying tag readers or optical sensors 220 may be implemented for example, through a window or a section of the tubing 228, through an RFID antenna disposed on a recess section of the tubing 228, through an optical sensor disposed in the tubing 228, or the like. The inline identifying tag readers or optical sensors 220 read, or otherwise sense, the passage of a carrier associated with the payload being transported through the pneumatic tube system.

In one embodiment of the present principles, the ID tags may be used to record the location and ID 114 and 122 of a carrier 610 at various locations throughout the pneumatic tube system 200 to send to the system control module 222 in order to keep a log of each carrier's location information as they move through the pneumatic tubing 228. This creates an auditable trail indicating a chain of custody. It allows the user to know where the carrier and its contents have been and where they are going.

While the present principles are described with respect to a hospital, the present principles may also be used in, but are not limited to, banks, retail stores, pharmacies, laboratories, or the like.

ID tags may also be associated with the ID of sending and receiving users. The ID tag scanning at the sending stations 224 and receiving stations 208 may be performed by an identifying tag reader such as, for example, a handheld PDA 700. However, any identifying tag reader 108 and 116 configuration may be used including, but not limited to, a scanner integrated into the sending or receiving station, or any other known or as yet undiscovered configuration.

System control module 222 may include database module 202 and computer control center module 206 in signal communication. The system control module 222 receives carrier information from the tag readers at the sending and receiving stations and logs the carrier information into a database module 202. Additionally, the system control module 222 may receive carrier location information from inline identifying tag readers or optical sensors 220 disposed throughout the pneumatic tube system 200 and log this information into a database manager 202.

The database module 202 may be, for example, a relational database, a flat file database, fixed length record database, or any other data storage mechanism known or as yet undiscovered in the art. Further, the database module 202 may reside on a stand-alone server, or the same machine as the computer control center module 206.

The computer control center module 206 manages data by interpreting data stored in the database module 202 and sending routing commands to the pneumatic tube system based on location data and delivery information collected from sending users. In one useful embodiment, the computer control center module 206 performs the functions of a data manager. In an alternative embodiment, there may be a separate data manager module to interpret the data stored in the database module 202 and send routing commands to the computer control center module 206 which then sends commands to the pneumatic tube system based on location data and delivery information.

The sending station 224, diverters 216 and 226, blower 214, carrier receiving bin 210, and receiving station 208 are all in signal communication with, and controlled by, the computer control center module 206. The computer control center module 206 interprets the data in the database module 202 and generates commands in the form of signals to individual elements in the pneumatic tube system 200 to control the actions of the system 200. For example, the computer control center module 206 may command the pneumatic tube system to activate the blower 214 to transport a carrier 610 through the pneumatic tube system 200. In response to data stored in the database module 202, the computer control center module 206 may generate a signal to turn on blower 214, which blows air to move the carrier 610 throughout the pneumatic tube system 200. Similarly, the diverters 216 and 226 may be signaled by the computer control center module 206 to route a carrier to a particular branch in the pneumatic transmission tubing 228 to be delivered to a desired receiving station 208.

The system control module 222 may also be configured to manage deliveries. The system control module 222 receives requests for delivery from a sending station 224. The data input by a user at a sending station 224 identifying tag reader 108 is used to determine the physical location of a carrier 610 and where the carrier 610 should be routed to. Additionally, the system control module 222 uses the information from the sending station 224 to determine how the carrier should be delivered (i.e. secured, with alarms, etc.).

System control module 222 may also track carriers 610 as they move past inline identifying tag readers or sensors 220 in the pneumatic tubing 228. The system control module 222 may generate records to show that a carrier 610 passed an inline identifying tag reader or sensor 220 at a certain time. These records may be used to ensure that carriers 610 are routed correctly and in the correct order. Location recordation may also be used to troubleshoot and initiate error notifications, such as a stuck or lost carrier 610, or may be used to guarantee or verify a timely delivery for perishable contents (i.e. drugs or blood contents that must be refrigerated). Additionally, reports on chain of custody of carriers may be generated to keep record of who has a specific carrier at a specific point in time and where that carrier is located.

The system control module 222 may also control and verify delivery to receiving users at receiving stations 208. In order to initialize a shipment, the sending user enters information into the sending station 224 that will be used to manage carrier 610 routing and delivery through the pneumatic tube system 200. The sending user prepares the contents of the carrier 610 for shipment. The contents of the carrier 610 may be, for example, prescriptions, blood samples, patient file information, and the like.

After the sending user prepares the contents of the carrier 610 for shipping from the product production station 232, the sending user may scan the ID of the carrier contents 110 with the handheld PDA 700. The sending user may also scan the sending user ID 112, the ID of the desired receiving station 106, and the ID of the carrier 114 with the handheld PDA 700.

In one useful embodiment, the sending user may work at a desk or station separate from the sending station and may place the carrier 610 on a conveyor belt at the product production station 232 to be delivered automatically to the sending station 224. The contents and the carrier 610 are brought to the sending station 224 via an incoming conveyor from the product production station 232. The product prepared by the sending user enters the carrier 610 through an opening in the top of the carrier 610. In one embodiment, a loaded carrier 610 may optionally be moved to an inspection station and subsequently sent into the pneumatic tube system 200 where it is delivered to the proper location in response to commands from the computer control center module 206. Alternatively, the contents and the carrier 610 may be deposited directly into the sending station 224 by the sending user without the aid of a conveyor belt or inspection station.

In another useful embodiment, a more passive system may be used for the scanning of the delivery information. The identifier tags may be RFID tags which can be read by an RFID identifying tag reader. In such an embodiment, the sending user at the sending station 224 may move near the RFID identifying tag reader while holding the carrier and its contents, and the reader will read and send the ID information from the sender, the carrier, and the contents to the system control module 222. Thus, sending users may advantageously avoid physically scanning each identifier tag to obtain delivery information.

The scanned information from the handheld PDA 700 is transmitted to the system control module 222 where it is stored in the database module 202 and interpreted by the computer control center module 206. The computer control center module 206 then determines the destination of a particular carrier 610, and the necessary command to route the carrier 610 properly. The computer control center module 206 sends routing commands to the pneumatic tube system 200 to control the operations of the system.

Blower 214 and diverters 216 and 226 may be used to coordinate and direct the transportation of the carriers throughout the pneumatic tube system 200 and between the storage compartment 218 and the pneumatic tube system 200. Carriers move through branches of the pneumatic tubing 228 in the system under vacuum or pressure supplied by blower 214. The computer control center module 206 sends a signal to the blower 214 to blow air to transport the carrier 610 at the appropriate time. As the carriers move through the system, the computer control center module 206 controls the carriers' 610 routing by transmitting commands to diverters 216 and 226 which may change the position and/or direction of the carriers 610. In an alternative embodiment, a vacuum system may be used in place of a blower 214 to move carriers 610 through the pneumatic tube system with negative air pressure.

In one embodiment, after the computer control center module 206 routes the carriers 610 through the tubing 228 via the diverters 216 and 226, the carriers 610 travel to the carrier receiving bin 210 at the receiving station. At this station, the carrier 610 is opened and the contents of the carrier 610 are dropped in the carrier receiving bin 210. The ID of the empty carrier 122 may then be scanned with the handheld PDA 700 to keep record of which carriers 610 are available from the storage compartment 218 for other shipments.

Upon receipt of the contents the receiving user may scan their ID 120, and may also scan the ID tags of the carrier contents 118. This information is sent to the system control module 222 where it is stored in the database module 202 and interpreted by the computer control center module 206. The computer control center module may optionally notify the sending user of completion of the transaction according to the sending user's instructions entered when the carrier was initially sent.

In an alternative embodiment, a slide plate 236 may be disposed in the pneumatic tubing 228 at a location prior to the carrier receiving bin 210. The slide plate 236 may be used as a security measure, holding the carrier 610 above the carrier receiving bin 210 until the authorized receiving user scans their ID 120. The sending user may be given the option by the handheld PDA 700 prior to sending the carrier 610 from the sending station 224 of requiring the receiving user to scan the receiving user ID 120 before retrieving the contents. If the sending user requires the receiving user to scan the receiving user ID 120, the computer control center module 206 will engage the slide plate 236 and hold the carrier 610 in the tube 228 above the carrier receiving bin 210 until the receiving user scans the receiving user ID 120. If the sending user does not require this security option, the carrier 610 will be allowed to move through slide plate 236 and into the carrier receiving bin 210. The inline identifying tag readers or optical sensors 220 disposed throughout the pneumatic tube system may also be associated with the slide plate because they are configured to sense the passage of the carrier and its contents through the pneumatic tubing until it reaches the slide plate. The inline identifying readers or optical sensors 220 may verify to the computer control center module that the carrier has arrived at the slide plate at which point the computer control center module may determine if a receiving user ID needs to be scanned.

In another embodiment, after each transaction is complete, the delivery information stored and recorded by the system control module 222 may be made accessible to users via a web browser. However, in alternative embodiments, this information may be accessible via stand-alone applications, hard copy documents, or any other useful report format. The delivery information may be used to audit compliance with delivery procedures, required time constraints, or to track any missing or problem deliveries.

Figure 3:
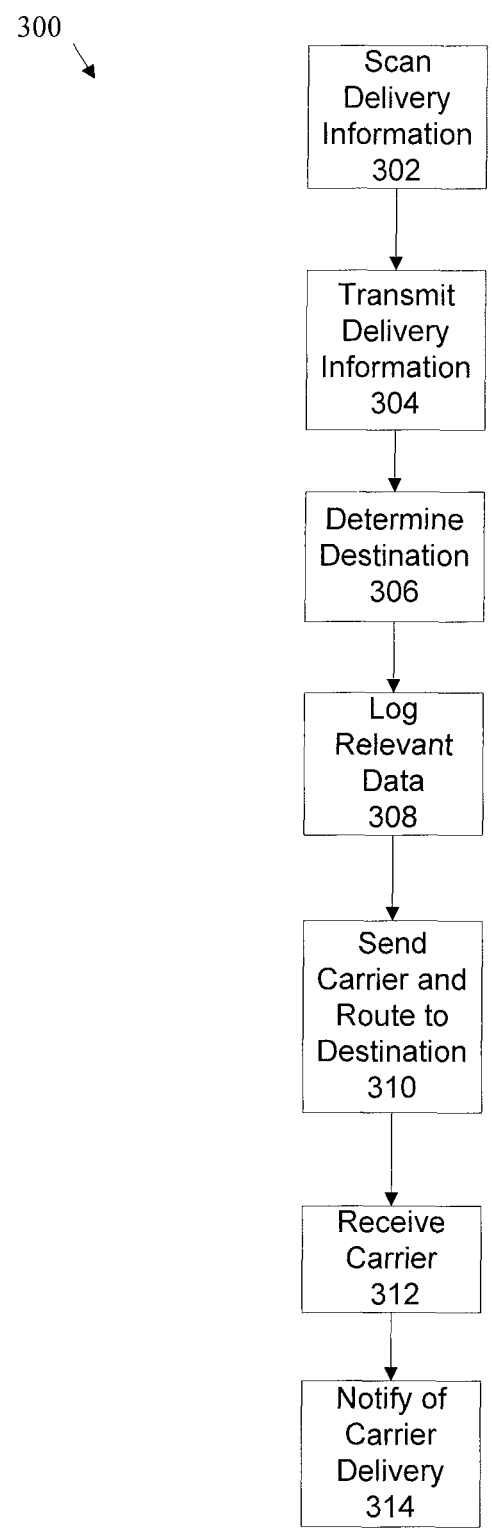
FIG. 3 is a flow chart illustrating a method for tracking carriers and payloads in a pneumatic tube system according to an embodiment of the present principles.

Referring now to FIG. 3, a flow chart illustrating a method 300 for tracking carriers and payloads in a pneumatic tube system 200 according to an embodiment of the present principles is shown. The sending user scans the delivery information in block 302. The identifying tag reader 108 disposed at the sending station 224 sends the information to the computer control center module 206 in block 304. The computer control center module 206 determines the physical destination of the carrier delivery in block 306. The data regarding the carrier delivery is then stored in the database module 202 in block 308. The computer control center module 206 sends commands to the elements of the pneumatic tube system 200 in block 310 to route the carrier and to engage or open the slide door 236. Finally, the receiving user receives the carrier 610 delivery in block 312 and notification of the carrier delivery is sent to the sending user in block 314.

Figure 4:
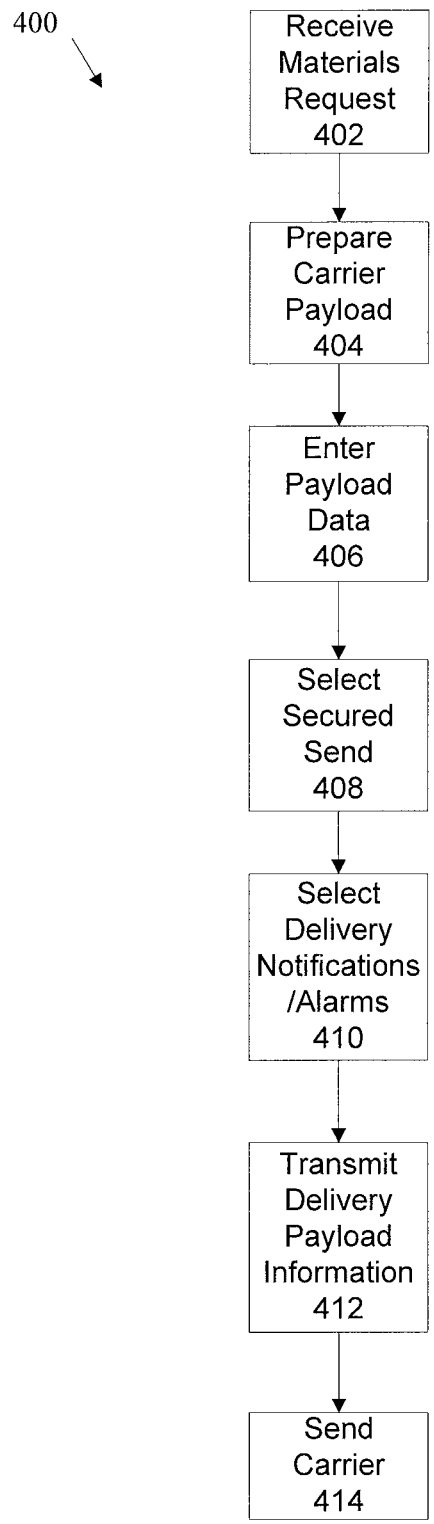
FIG. 4 is a flow chart illustrating a method of preparing and sending carriers and payloads from the sending station according to an embodiment of the present principles.

Referring now to FIG. 4, a flowchart illustrating a method of preparing and sending carriers and payloads 400 from the sending station 224 according to an embodiment of the present principles is shown. The sending user receives a request for a delivery (i.e. a prescription, blood sample, file information, or the like) in block 402. The sending user prepares the contents and requests a carrier 610 from the storage compartment 218 of the pneumatic tube system 200 via the handheld PDA 700 in block 404. Upon receipt of the carrier 610, the sending user may scan the carrier ID 114, content ID 110, the sending user's ID 112, the sending station ID 104, or the receiving station ID 106 using the identifying tag reader 108 in block 406. The sending user may optionally require the receiving user to scan the receiving user ID 120 before the carrier 610 moves to the carrier receiving bin 210 in block 408. If the sending user requires the receiving user to scan their ID 120 before the carrier 610 moves to the carrier receiving bin 210, then the sending user has the option of being notified if the receiving user ID 120 is not scanned after the carrier 610 moves to the carrier receiving bin 210 and to the receiving station 208. If the sending user chooses to be notified then they may select an alarm for notification from the handheld PDA 700 in block 410.

The sending user also has the option of being notified, for example, when the carrier 610 arrives at the receiving station 208, gets stuck in a tube 228, or contents have been spilled. If the sending user chooses to be notified when the carrier arrives at the receiving station 208, gets stuck in the tube 228, or contents have been spilled, then he/she selects a notification. If not, then in one embodiment, the sending user places the carrier 610 on the conveyor belt.

The sending user may send the carrier by pressing the send button on the handheld PDA 700. To send a carrier, the delivery information is sent to the system control module 222 in block 412. In response, the system control module 222 controls the pneumatic tube system to move the carrier 610. The carrier 610 leaves the sending station 224 and enters the pneumatic tube system 200 in block 414.

Figure 5:
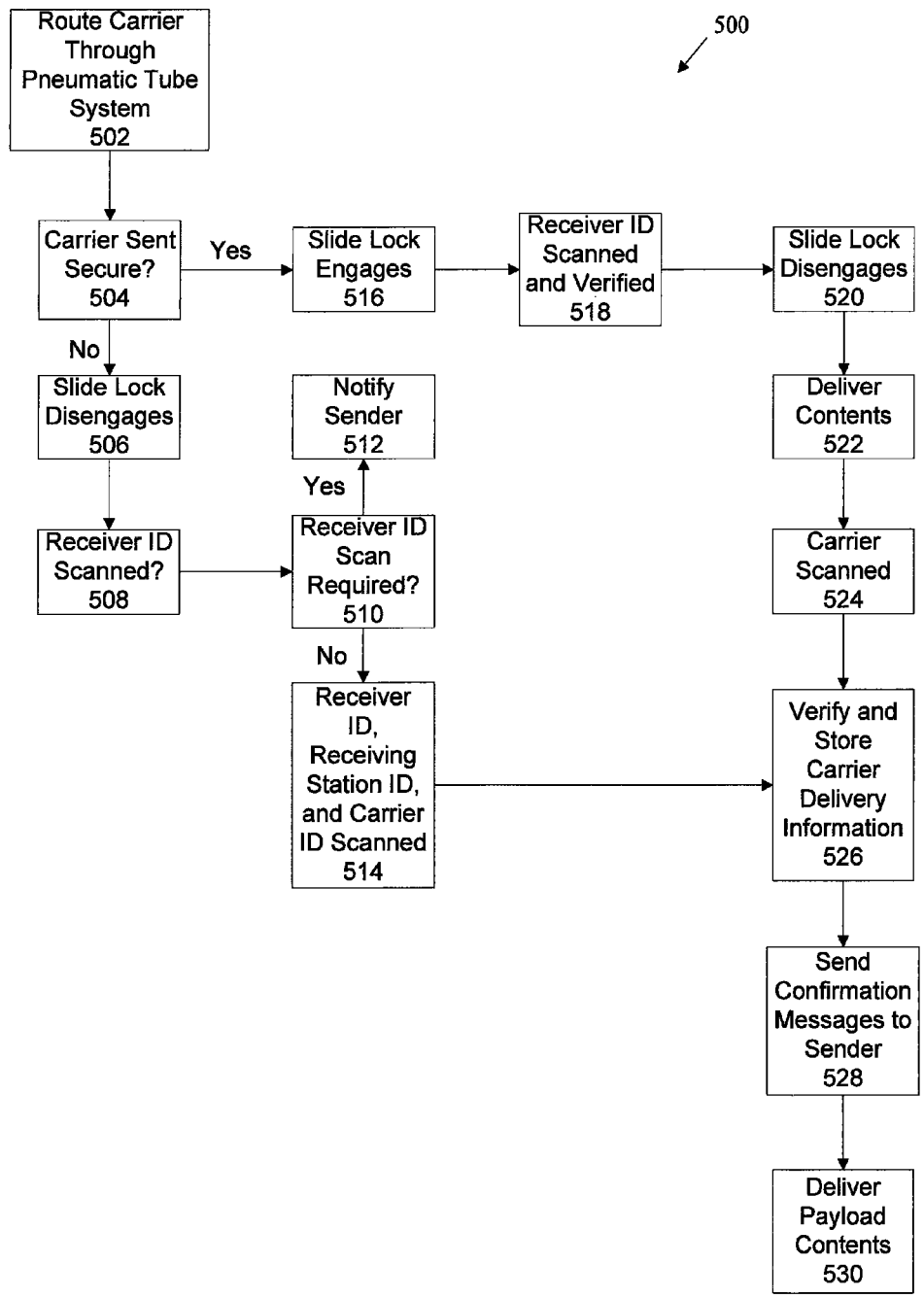
FIG. 5 is a flow chart illustrating a method of receiving the carriers and payloads from the receiving station according to an embodiment of the present principles.

Referring now to FIG. 5, a flowchart illustrating a method for receiving carriers and payloads 500 from the receiving station 208 according to an embodiment of the present principles is shown. The carrier 610 travels through the pneumatic tube system 200 in block 502 until the carrier 610 reaches the slide plate 236, and is retained at, or passed though, the slide plate in response to commands from the system control module in block 504.

If the sending user did not request that the receiving user scan their ID 120 before the carrier 610 reaches the carrier receiving bin 210, then the slide door opens in block 506, allowing the carrier 610 to move through to the carrier receiving bin 210 at the receiving station 208. The system control module 222 then determines whether or not the receiving user ID 120 was scanned in block 508.

If the receiving user ID 120 was scanned then the receiving user continues to scan the receiving station ID 106 and carrier ID 122 in block 514. If the receiving user ID is not scanned then the system control module 222 determines if the sending user requested notification if the receiving user ID 120 is not scanned in block 510. If the sending user requested notification than the system control module 222 sends an alarm notifying the sending user in block 512. If the sending user did not request notification then the receiving user scans the receiving station ID 106 and carrier ID 122 in block 514 and selects the accept button on the handheld PDA 700. The system control module 222 then verifies and stores the delivery information in block 526 and sends a confirmation message to the sending user in block 528. The contents 110 of the carrier 610 are then delivered to the end user in block 530.

If the sending user requests that the receiving user scan their ID 120 before the carrier 610 reaches the carrier receiving bin 210, then the system control module 222 engages the slide plate 236 in block 516, holding the carrier 610 in the pneumatic tubing 228. The receiving user must then scan their ID 120 and the receiving station ID 106 in block 518 in order to disengage the slide plate 236. After the receiving user ID 120 is scanned, the computer control center module 206 verifies the user ID before unlocking the slide plate 236. After verification, the computer control center module 206 commands the slide plate 236 to disengage. The receiving user then selects the drop carrier button on the handheld PDA and the slide plate 236 disengages in block 520, moving the carrier 610 through to the carrier receiving bin 210 and to the receiving station 208 in block 522. The receiving user scans the carrier ID 122 in block 524. The system control module 222 then verifies the delivery information in block 526 and if selected by the sending user, a confirmation message is sent to the sending user in block 528. The delivery information is sent to be stored in the database module 202 and the contents are delivered to the end user by the receiving user in block 530.

Referring now to FIG. 6A, a diagram of the carrier 610 with a unique identifying, optically scannable, tag (i.e. a bar code) 620 according to an embodiment 600 of the present principles is shown. The bar code 620 may be disposed on any part of the carrier 610, enabling the inline identifying tag readers 220 to scan the bar code 620 and transmit the delivery information and reception information to the system control module 222.

Figure 6B:
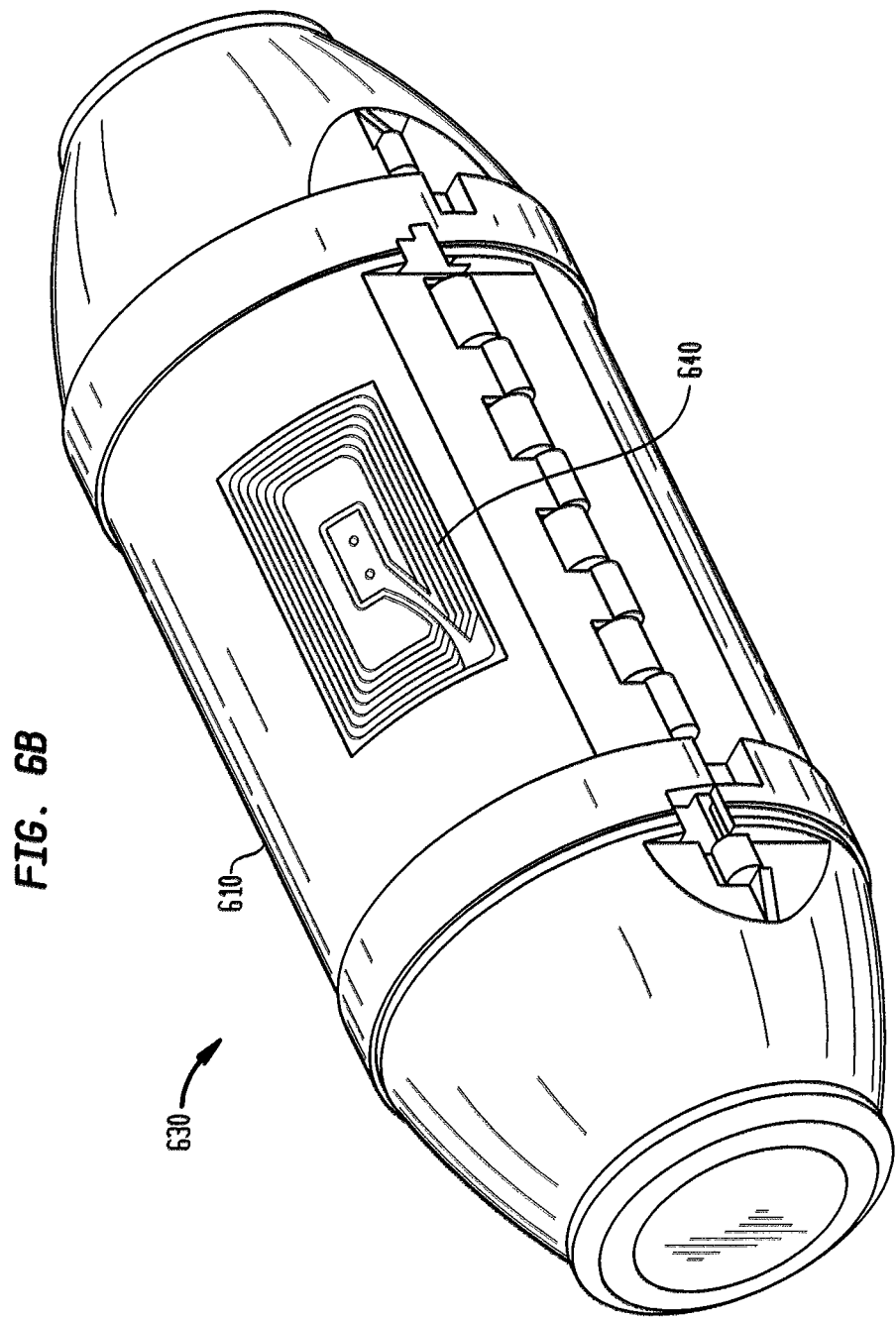
FIG. 6B is a diagram of a carrier having a Radio Frequency Identification ("RFID") tag according to an embodiment of the present principles.

Referring now to FIG. 6B, a diagram of the carrier 610 with a unique identifying RFID tag 640 according to an embodiment 630 of the present principles is shown. The RFID tags 640 may be disposed on any part of the carrier 610, enabling the inline identifying tag readers 220 to scan the RFID tags 640 and transmit the delivery information and reception information to the system control module 222.

Figure 7A:
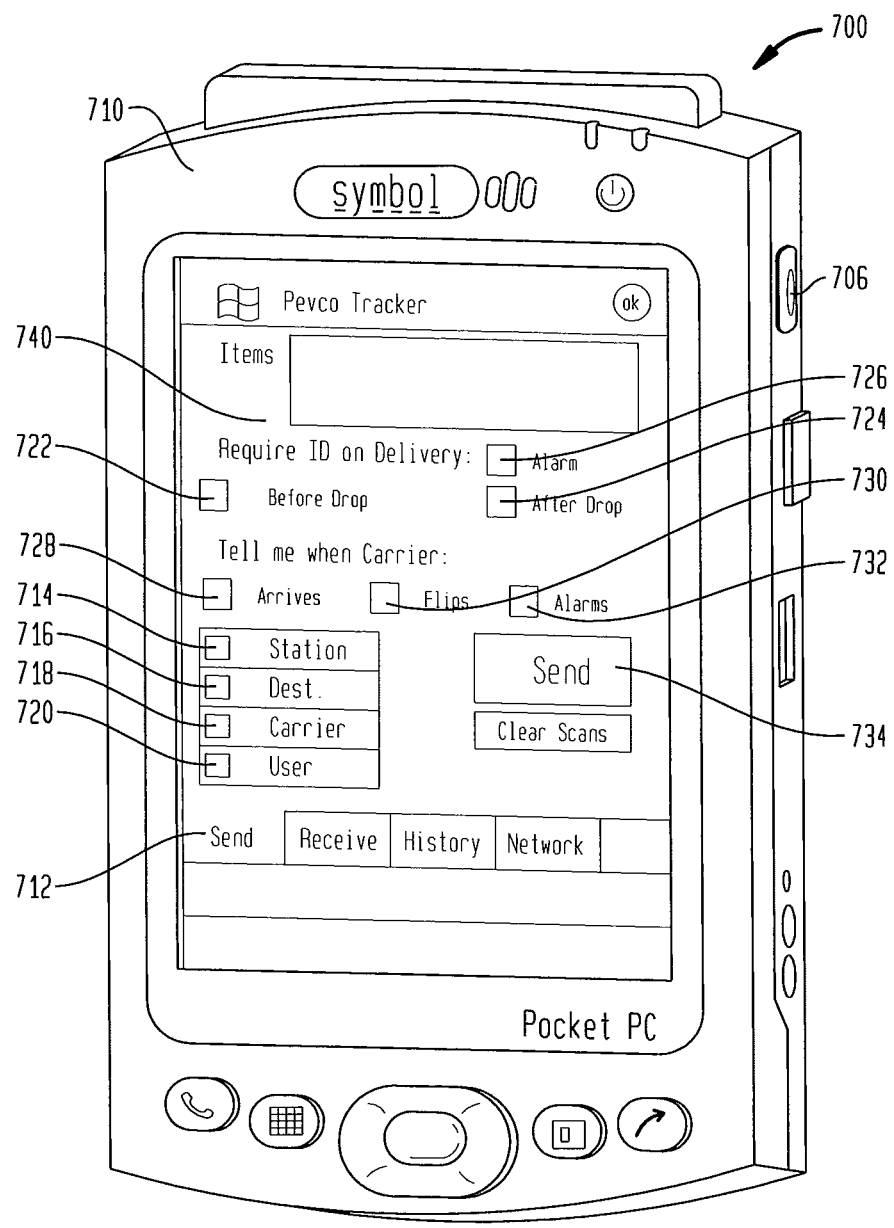
FIGS. 7A and 7B are diagrams of a handheld PDA Reader according to an embodiment of the present principles.
Figure 7B:
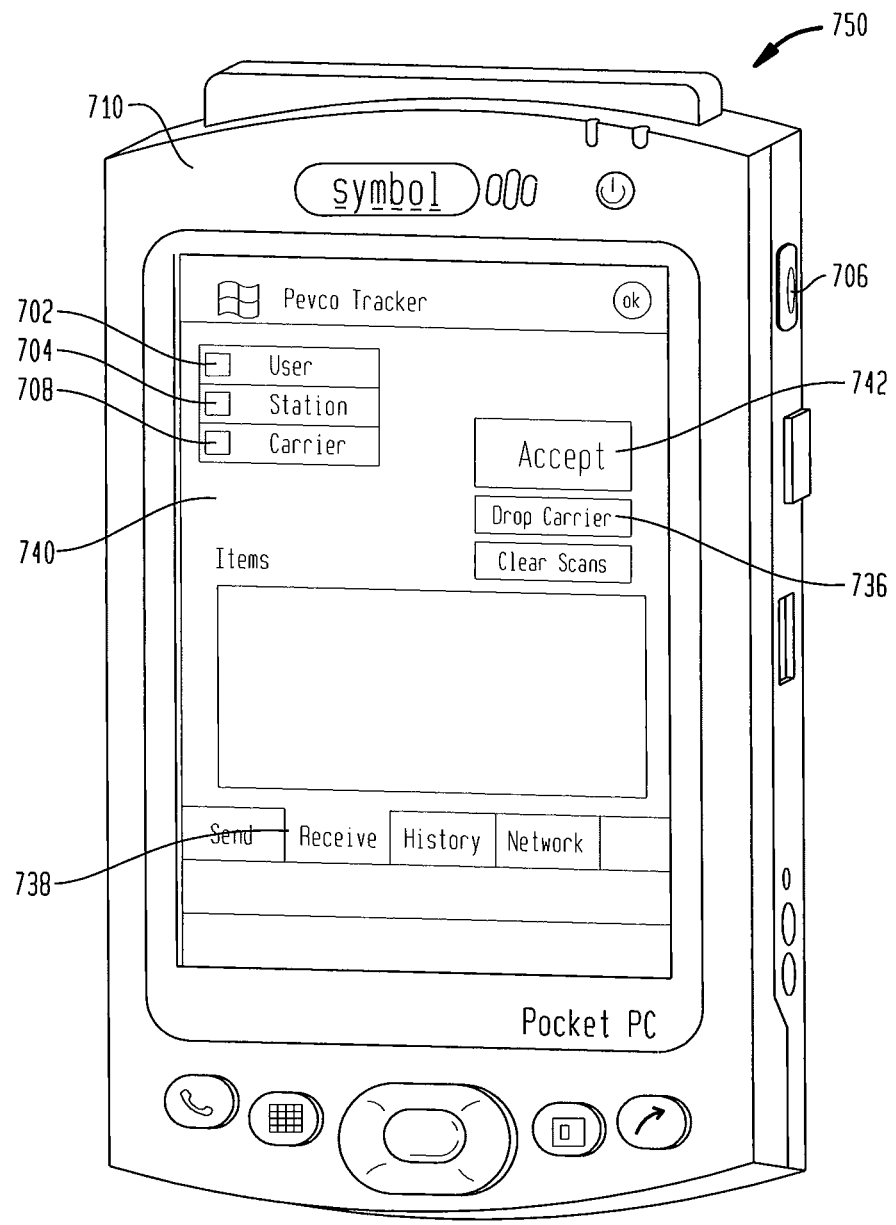

Referring now to FIGS. 7A and 7B, a handheld PDA 700 configured for use as an identifying tag reader and user interface according to an embodiment of the present principles is depicted. While the handheld PDA 700 is described as a useful embodiment of the present principles, it is only exemplary of an identifying tag reader that may be used. For example, a non-handheld PDA may be used, in addition to a touch key initialization module attached to a wall, etc.

The handheld PDA 700 is provided to capture and present data associated with sending and receiving pneumatic tube system deliveries. The PDA allows the user to perform operations required to send and receive a carrier delivery transaction without requiring an interface built into each station. The handheld PDA 700 may capture unique identifiers (bar codes, RFID tags, or the like) associated with individual carriers, sending stations, receiving stations, and sending and receiving users to help track the delivery information.

The database module 202 and computer control center module 206 may provide notification to a sending user's cell phone, PDA, e-mail, etc., regarding delivery details as well as providing notification to receiving users of incoming carriers based on options chosen from the handheld PDA 700. The handheld PDA 700 may further provide options for secure sending, such as holding a carrier at a station slide plate 236 until the receiving user scans their ID.

The handheld PDA 700 provides real-time information to users. This information transmitted from the handheld PDA 700 and stored in the database module 202 may be password protected and accessible through a web browser or any other useful interface. Handheld PDA 700 is capable of collecting many types of information, including but not limited to the sending user's ID, the content's ID, the carrier's ID, the sending station's sent ID, the receiving station's ID, the time the transaction was requested, the time the carrier left the station, the travel time to carrier destination, the transaction number, whether or not it is a secure send, whether or not an alarm has been chosen, the alarm type if chosen, the time the carrier arrived at its destination, the receiving user's ID, the time the carrier was scanned upon arrival, and the receiving station ID. While the handheld PDA 700 has at least these capabilities, any combination of these capabilities may be used to track and record delivery information and reception information.

The steps of using the handheld PDA 700 from the sending user's station 224 can be described in reference to FIG. 7A. In one embodiment, in order to initialize a transaction, the sending user first selects the "Send" tab 712 on face 710 of handheld PDA 700. The sending user then scans the sending station ID 104. In one useful embodiment, the scan may be initiated by pressing the scan button 706 on either side of the PDA 700 while holding the PDA 700 up to the unique identifying tags (i.e. bar code, RFID, optical sensor, etc.) used for the sending station ID 104. A check-mark at "Station" 714 may indicate that the sending station ID 104 has been properly scanned. The sending user may scan the receiving station ID 106 and the interface 740 may indicate that "Dest." 716 or the receiving station ID 106 has been properly scanned. Next, the sending user may also scan the carrier ID 114 and the interface 740 may indicate, by showing a check-mark in the box next to "Carrier" 718, that the carrier ID 114 has been properly scanned. The sending user may also scan the carrier contents 110 and the sending user ID 112. The interface 740 may indicate, by a check-mark in the box next to "User" 720, that the sending user ID 112 has been properly scanned.

The sending user then has the option of securely sending the carrier 610 by requiring the receiving user to scan the receiving user ID 120 before or after the carrier 610 drops into the carrier receiving bin 210. If the sending user desires that the receiving user scan their ID 120 before the carrier 610 is delivered, then the sending user may select the "Before Drop" 722 button. A check-mark may appear in the box next to "Before Drop" 722 to indicate that this option has been selected. If the sending user desires that the receiving user scan their ID 120 after the carrier 610 drops, then the sending user chooses the "After Drop" 724 button and the interface 740 may indicate via a check-mark in the box next to "After Drop" 724 to show that this option has been selected.

If the sending user chooses "After Drop" 724, the sending user also has the option of selecting "Alarm" 726 to be notified if the receiving user does not scan their receiving user ID 120 after the carrier 610 drops. A check-mark may appear in the box next to "Alarm" 726 to indicate that this option has been selected. Further, the sending user can choose to be notified when the carrier 610 "Arrives" 728, "Flips" 730, or "Alarms" 732. A check-mark next to an appropriate label may indicate which options have been selected. The sending user may also send the carrier 610 by selecting the send button 734 to complete the transaction.

The steps of using the handheld PDA 700 from the receiving station 208 can be described in reference to FIG. 7B. In order to receive a carrier delivery the receiving user first selects the "Receive" tab 738 on the face 710 of handheld PDA 700. Alternately, the system control module 222 may notify the receiving user that a carrier 610 has arrived. The receiving user may scan any ID, such as their user ID or the carrier ID, by pressing the scan button 706 on either side of the PDA 700 while holding the PDA 700 up to the unique identifying tags. A check-mark may, for example, appear in the interface 740 of the PDA 700 in the box next to "Station" 704 to show that the receiving station ID 104 has been properly scanned or the interface 740 may indicate by a check-mark in the box next to "User" 702 to show that the receiving user ID 120 has been properly scanned and "Carrier" 708 to show that the carrier ID 122 has been properly scanned. The receiving user may also select the "Drop Carrier" 736 button to manually release the carrier 610 into the carrier receiving bin 210 in the receiving station 208.

The receiving user may initiate the recordation of a received carrier by selecting the "Receive" tab 738. The receiving user may scan the receiving station ID 106, the receiving user ID 120 or carrier ID 122. The user interface on the PDA may show, via, for example, a check-mark next to the "Station" 704, "User" 702 and "Carrier" 708 icons to indicate that the associated ID has been properly scanned. The receiving user may select the "Accept" 742 button on the user interface 740 to complete the transaction. The sending user may receive a confirmation message that the carrier 610 was delivered if that option was selected when the carrier 610 was sent. While in one useful embodiment a check mark may be used as an indicator of selections and properly scanned IDs, any other indicator may be used without deviating from the scope of the invention. For example, an "x" may indicate that an ID was properly scanned, an ID or selection may be highlighted to indicate that it was properly scanned, or any other interface may be used that is known in the art or as yet undiscovered.

While the interface for the PDA 700 is described herein as having a specific type of interface for reading specific types of IDs and permitting the user to interact with the tracking system, any interface permitting a user to interact with the tracking system may be advantageously disposed on the PDA 700 or on any other input element. Likewise, while the PDA 700 may actively read ID tags, such as bar codes or optical codes, the PDA 700 may also passively read RFID tags or other radio frequency identifiers, or may use any combination of passive and active ID detection. For example, a user may have an RFID badge that is passively read while the carrier may have an optical ID tag that is actively read. In another useful embodiment, the PDA 700 may be associated with a particular user, sending station, receiving station, or the like, the ID for which is stored in the PDA 700 or elsewhere in the tracking system for recall when a user sends a payload. In such an embodiment, the PDA 700 may automatically attribute the stored user ID, sending station ID, or receiving station ID to the outgoing payload.

Figure 8:
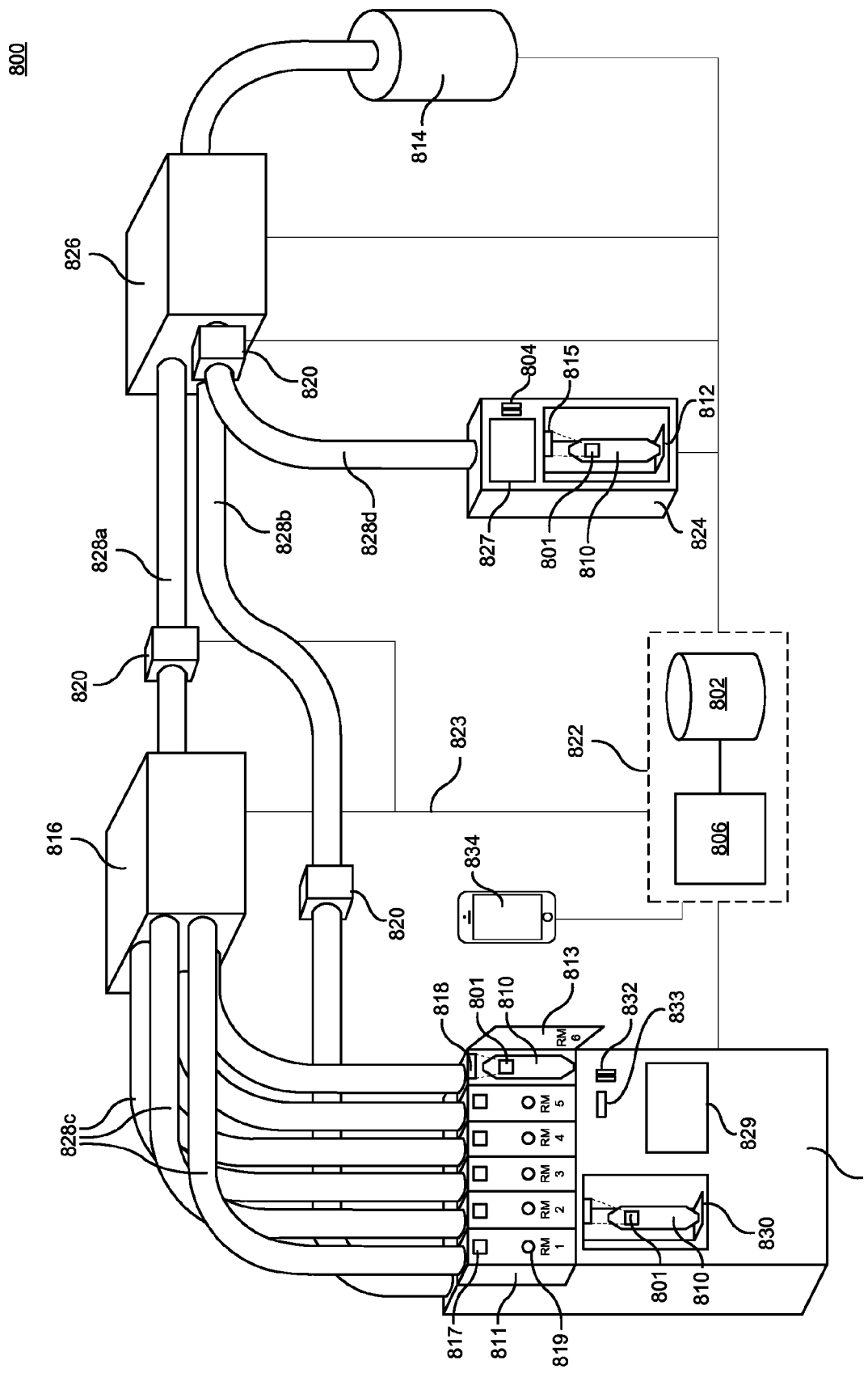
FIG. 8 is a diagram illustrating a pneumatic tube system according to another embodiment of the present principles.

Referring to FIG. 8, a diagram illustrating a pneumatic tube system 800 according to another embodiment of the present principles is shown. The pneumatic tube system 800 utilizes, in one non-limiting embodiment, a sending station 824 and a receiving station 808, for sending and receiving pneumatic carriers, such as carrier 810. Stations 824 and 808 connect to a pneumatic tube system 800 via transmission tubing 828*a-d* and communications capability 823. The system also includes blower 814 that blows air into pneumatic tubing 828*a-d* to move the carrier 810 throughout the pneumatic tube system 800. The system further includes one or more diverters 816 and 826 which direct the transportation of carriers 810 from sending station 824 to receiving station 808 at the direction of the system control module 822. The configuration of the pneumatic tube system 800 shown in FIG. 8 is only exemplary. The pneumatic tube system 800 of the present invention can comprise any number of sending and receiving stations and diverters as required. In a preferred embodiment, system 800 is utilized in a hospital setting for delivering prescription from a pharmacy to the patient. Accordingly, system 800 may utilize a single sending station 824 located at the pharmacy of the hospital and a plurality of receiving stations 808 each preferably located at each nursing station throughout the hospital. This enables system 800 to deliver prescriptions from the sending station 824 to any nursing station within the hospital equipped with a receiving station 808. While the present principles are described with respect to a hospital, the present principles may also be used in, but are not limited to, banks, retail stores, pharmacies, laboratories, or the like.

System control module 822 controls the operation of pneumatic tube system 800, reading, storing, and presenting data, and tracking the delivery of carriers in response to the collected data. System control module 822 may include database module 802 and computer control center module 806 in signal communication. The sending station 824, diverters 816 and 826, blower 814, and receiving station 808 are all in signal communication with, and controlled by, the computer control center module 806. The database module 802 may be, for example, a relational database, a flat file database, fixed length record database, or any other data storage mechanism known or as yet undiscovered in the art. Database module 802 may reside on a stand-alone server, or the same machine as the computer control center module 806. The computer control center module 806 interprets the data in the database module 802 and generates commands in the form of signals to individual elements in the pneumatic tube system 800 to control the actions of the system 800.

In a preferred embodiment, sending station 824 is located within a pharmacy to deliver prescriptions to hospital patients. Sending station 824 may contain touch screen 827, which allows for user input and communication. Preferably, touch screen 827 has at least the same interface functionality of PDA 700. Touch screen 827 allows a user to identify the destination for the carrier and input any other instructions for the handling of the carrier. Instructions may include options such as "Before Drop", "After Drop", "Arrives", "Flips" or "Alarms" options, and the user may request notification if the carrier gets stuck in a tube or the contents have spilled. In an alternative embodiment, the functions of touch screen 827 may be accomplished using manual buttons, switches or other controls, in which event a screen without touch capability may be used.

Station 824 also contains a card reader 804. Card reader 804 may read and store information from a unique ID card associated with the carrier contents or payload, the sending user's ID card, the receiving user's ID card, or a unique ID card associated with the carrier itself. The card reader 804 may also read and store information from a unique ID card associated with the sending station and/or delivery station. Preferably, card reader 804 is designed to read cards swiped through the card reader 804. In alternative embodiments, card reader 804 may read the ID card of objects using an optical scanning system to read bar codes, characters or other objects. The card reader 804 may identify objects using RFID or other radio frequency technology, and may actively or passively read cards. Additionally, any other identification technology known, or as yet undiscovered, may be used within the scope of the present principles.

Station 824 also contains a tag reader 815. Tag reader 815 may read and store a unique ID tag 801 associated with the carrier ID disposed on pneumatic carrier 810, or unique ID tags associated with the carrier contents or payload, the sending user's ID, or the receiving user's ID. The tag reader 815 may also read and store a unique ID tag associated with the sending station, the receiving station, and/or the receiving bin of the receiving station (as will be later described). Preferably, tag reader 815 is designed to read the ID tag of objects using an optical scanning system to read bar codes, characters or other objects. The tag reader 815 may identify objects using RFID or other radio frequency technology, and may actively or passively scan IDs. Additionally, any other identification technology known, or as yet undiscovered, may be used within the scope of the present principles.

Preferably, card reader 804 and tag reader 815 are affixed to station 824. Alternatively, card reader 804 and/or tag reader 815 may be embodied in a handheld device in signal communication with station 824. Handheld device may comprise a portable or mobile communication device, a cellular phone, a smart phone, a tablet computer, a mini tablet computer, and any handheld device known in the art.

Sending station 824 further contains a carrier receiving bin 812 for receiving a pneumatic carrier 810. Station 824 is in signal communication with the system control module 822, and information is communicated between station 824 and system control module 822.

In an alternative embodiment, sending station 824 may be located within a fully automated pharmacy, as described in U.S. Pat. No. 6,202,004, the entire contents of which is hereby being incorporated by reference. The product prepared by the automated pharmacy may be delivered to the sending station 824 via a conveyor belt. Sending station 824 automatically scans the ID tag on the product using tag reader 815 and transmits this information to the system control module 822 to determine the appropriate station to send the product based upon information associated with the product ID. At the sending station 824, the product is automatically loaded into a carrier 810, inserted into the receiving bin 812 of the sending station 824, and routed to the correct location.

Sending station 824 may also be connected via network to other information systems. In a hospital environment, station 824 can be linked to other hospital systems such as pharmacy management, laboratory management and security management systems. Such communication may be made by wired or wireless connection, packet-switched network, or other communications system. In this regard, information from the pneumatic tube system may be integrated into a larger hospital system, and information from the hospital system may be used by station 824 and other elements of the system.

Lights or speakers may be included in, or connected to, station 824. These may be used to notify users that a carrier has been received, that an error has occurred, that maintenance is required, or for any other suitable purpose.

In a preferred embodiment, each nursing station at a hospital includes a receiving station 808 for receiving patient prescriptions. Like sending station 824, receiving station 808 may comprise a touch screen 829, a card reader 832, and one or more tag reader 833. Each receiving station 808 preferably comprises a plurality of receiving bins 811, each for receiving a pneumatic carrier 810. Receiving station 808 is shown to contain six receiving bins 811, however, any number of receiving bins may be included in the receiving station 808 without departing from the scope of the present invention. Preferably, the number of receiving bins 811 is associated with the number of patient rooms handled by the nursing station. So if there are six patient rooms, the receiving station 808 will comprise six receiving bins 811. In another embodiment, the number of receiving bins 811 is associated with the number of patient beds handled by the nursing station.

Each receiving bin 811 may comprise a tag reader 818 for detecting the presence of a carrier 810 in the carrier receiving bin 811. Tag reader 818 detects the presence of the carrier 810 by scanning the ID tag 801 of the carrier. Tag reader 818 sends a signal to the station 808 and/or system control module 822 indicating that the carrier 810 has arrived at the receiving bin 811. Alternatively or in addition, each receiving bin 811 contains a presence sensor, such as a pressure sensor, to detect presence of the carrier and activate tag reader 818. Each receiving bin 811 may further comprise a visual indicator 819 on the exterior of the receiving bin 811 to visually display that a carrier has arrived at the receiving bin 811. The visual indicator 819 may be activated upon the detection by the tag reader 818 and/or a presence sensor of the presence of the carrier 810. Visual indicator 819 may comprise a light, a colored light (e.g., a green light), a flashing light, or the like.

In a preferred embodiment, each receiving bin 811 comprises a door 813 for preventing access to the receiving bin 811 by unauthorized users. The door 813 may be a hinged door, a sliding door, a bi-fold door, a telescoping door, or any other door known in the art. The door comprises a lock which is controlled by the receiving station 808 and/or the system control module 822. Any lock known in the art may be used, such as a turn lock, an electromagnetic lock, or the like. The door 813 may be unlocked by an authorized user in a number of ways. The user may use the touch screen 829 to enter user identifying information and identify the bin 811 of the plurality of bins the user wishes to unlock. The user may swipe a user ID card using card reader 832 and select the bin 811 the user wishes to unlock using the touch screen 829. The user may utilize a mobile communication device 834 preloaded with an application to select the bin 811 the user wishes to unlock as well as to enter user identifying information. Each door may comprise an ID tag 817 in a form of a barcode, a RFID tag, or the like, which the user may scan with the mobile communication device 834. In an alternative embodiment, each door 813 may be equipped with a scanning device or a sensor 817. A user may carry an ID tag preloaded with user information that may be scanned by the door scanning device or a sensor 817 to unlock the particular door 813. Regardless of the means used to unlock the door, the selected bin information and the user identification information is sent via the receiving station 808 or the mobile communication device 834 to the system control module 822 which determines whether the user is authorized to unlock the particular bin 811. System control module 822 may store a list or a log of authorized users allowed to unlock a particular bin such that only designated users may be allowed to unlock certain bins. For example, a head nurse in charge of the nursing station may have access to any one of the bins 811 of the receiving station 808. However, a nurse or a doctor that only attends a patient associated with only one of the bins will have access to that one particular bin, but not the other bins of the receiving station 808. The system control module 822 receives the selected bin information and the user identification information and determines whether the user is authorized to unlock the particular bin 811. If so, the system control module instructs the receiving station 808 to unlock the particular bin 811. The system control module 822 may log in database 802 that a particular user has unlocked the particular bin to retrieve the delivered carrier 810 for chain of custody purposes.

Receiving station 808 may further contain a separate carrier receiving bin 830 for dispatching empty pneumatic carriers 810 back to the sending station 824 via pneumatic tubing 828b and 828d and diverter 826. When the system is free from delivering carriers from sending station 824, it may return empty carriers 810 from separate carrier receiving bin 830 to the sending station 824. In addition, separate carrier receiving bin 830 may be used to send carriers 810 from the receiving station 808 to other stations of the pneumatic tube system 800 via pneumatic tubing 828b and additional tubing and diverters. In another embodiment, a separate zone, with a separate blower, diverter(s), and pneumatic tubing may be used to return empty carriers from receiving station 808 to a separate receiving bin at the sending station 824, thus not disturbing the flow of carriers from the sending station 824 to any receiving station 808 and any receiving bin 811 of the receiving station 808.

Pneumatic tube system 800 preferably comprises diverter 816 in direct communication with the receiving station 808 for directing the pneumatic carriers 810 to an appropriate receiving bin 811. Diverter 816 preferably comprises a single inlet port in communication with the sending station 824 via one or more tubing 828a and 828d and one or more diverters 826 for receiving a pneumatic carrier 810. Diverter 816 further comprises a plurality of outlet ports each in communication with a selected receiving bin 811 via tubing 828c for delivery of a carrier 810 to a particular receiving bin 811. Diverter 816 may be any diverter known in the art. It is in communication with and controlled by the system control module 822 for routing of the carrier to the appropriate outlet port.

Furthermore, pneumatic tube system 800 may include a plurality of inline identifying tag readers or optical sensors 820 configured to track or sense the carriers as they are transported through the tubing 828a-d. The inline identifying tag readers or optical sensors 820 may be implemented for example, through a window or a section of the tubing 828a-d, through an RFID antenna disposed on a recess section of the tubing 828a-d, through an optical sensor disposed in the tubing 828a-d, or the like. The inline identifying tag readers or optical sensors 820 read, or otherwise sense, the passage of a carrier associated with the payload being transported through the pneumatic tube system. The ID tags may be used to record the location and ID 114 and 122 of a carrier 810 at various locations throughout the pneumatic tube system 800 to send to the system control module 822. The system control module 822 receives carrier information from the tag readers at the sending and receiving stations as well as from inline identifying tag readers or optical sensors 820 and logs the carrier information into a database module 802 in order to keep a log of each carrier's location information as they move through the pneumatic tubing 828. This creates an auditable trail indicating a chain of custody. As described above, the carrier information from the various tag readers enable the system control module 822 to manage deliveries, determine how the carrier should be delivered (i.e. secured, with alarms, etc.), track carriers 810 as they move past inline identifying tag readers or sensors 820 in the pneumatic tubing 828a-d, generate records to show that a carrier 810 passed an inline identifying tag reader or sensor 820 at a certain time, and generate reports on chain of custody.

Advantageously, the pneumatic tube system 800 of the present invention allows for a series of carriers 810 to be sent simultaneously in series from the sending station 824 to the receiving station 808 (or a plurality of receiving stations 808). Upon approach to the diverter 816, the carrier ID tag 801 of a first carrier 810 in series may be scanned at the inlet port of the diverter 816 by an inline tag reader 820. The carrier ID information may be sent to the system control module 822, which may direct the diverter 816 to dispatch the carrier 810 to the appropriate receiving bin 811. Then the second carrier 810 in series would be scanned at the inlet port of the diverter 816 by the inlet tag reader 820 and be dispatched to an appropriate receiving bin 811 in the same manner, and so forth.

The pneumatic tube system 800 of the present invention effectively allows a drug to be delivered directly from the pharmacy to the patient. The architecture of the pneumatic tube system 800 allows for the creation of a complete chain of custody of a drug or any other payload from the pharmacy to the patient. It also enables the isolation of drugs between patients reducing errors of administering drugs to the wrong patient and improving patient security. Using the pneumatic tube system 800, the patient may be billed directly for the prescribed drug. To effectively and securely deliver content in pneumatic tube system 800, database 802 of the pneumatic tube system 800 may store files associated with each patient, and preferably with the patient's unique ID accorded to the patient during admission to the hospital. Each file may include, for example:

1. Patient ID;
2. Name of the patient;
3. Room number of the patient;
4. Bed number of the patient;
5. Receiving station ID associated with the patient;
6. Receiving bin ID associated with the patient;
7. Name, strength, and diluent of drug to be delivered to the patient; and
8. IDs of authorized users allowed access to the receiving bin associated with the patient.

Database 802 may store additional information or less of the above listed information without departing from the scope of the present invention. The system control module 822 uses the above information to properly route drugs from the sending station to the receiving bin associated with the patient. During delivery the system control module 822 will also keep a log of chain of custody of the drug based on the information collected before, during, and after transportation.

Figure 9:
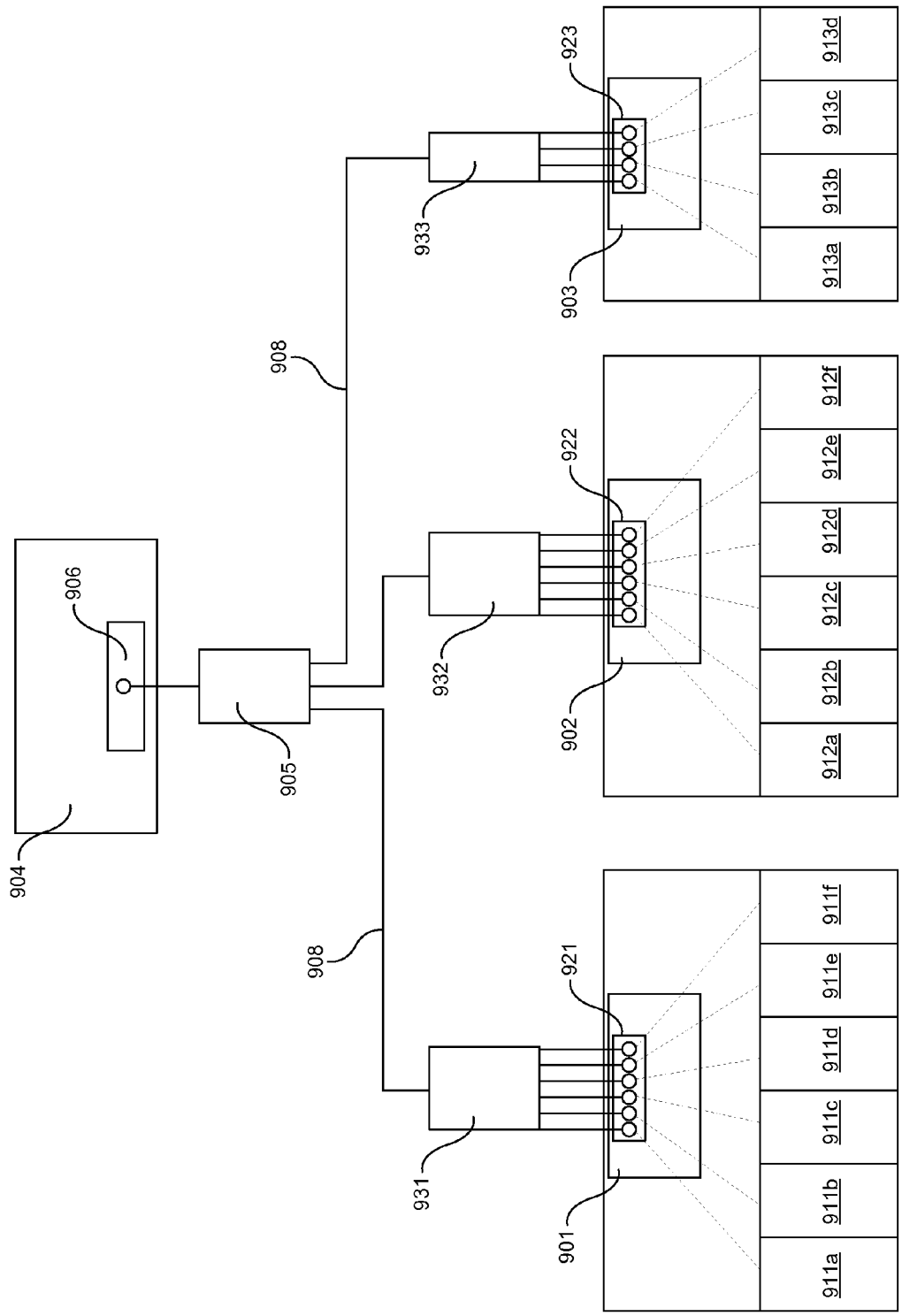
FIG. 9 is a schematic diagram illustrating the pneumatic tube system in FIG. 8 in a hospital environment according to an embodiment of the present principles.

As discussed above, the present invention may be scaled to any desired size. FIG. 9 illustrates an exemplary embodiment of the pneumatic tube system 900 of present invention in a hospital. As shown, the hospital may include a sending station 906 within a pharmacy 904 in a separate building connected via pneumatic tubing 908 to a plurality of nursing stations 901, 902, and 903 within the hospital. Each nursing station 901, 902, and 903 may be located in a wing in charge of a plurality of rooms. For example, nursing station 901 may be in charge of six rooms 911a-911f, nursing station 902 may be in charge of six rooms 912a-912f, and nursing station 903 may be in charge of four rooms 913a-913d. Each nursing station 901, 902, 903 will include a receiving station 921, 922, 923, respectfully, comprising a plurality of receiving bins corresponding to the number of rooms in the wing of the nursing station. As such, nursing station 901 comprises receiving station 921 comprising six bins connected to a six port diverter 931, nursing station 902 comprises receiving station 922 comprising six bins connected to a six port diverter 932, and nursing station 903 comprises receiving station 923 comprising four bins connected to a four port diverter 933. Diverters 931, 932, and 933 are connected to sending station 906 via diverter 905. Each bin corresponds to the respective room associated with the nursing station, such that drugs for a particular patient are delivered to the bin associated with the room occupied by the patient.

Figure 10:
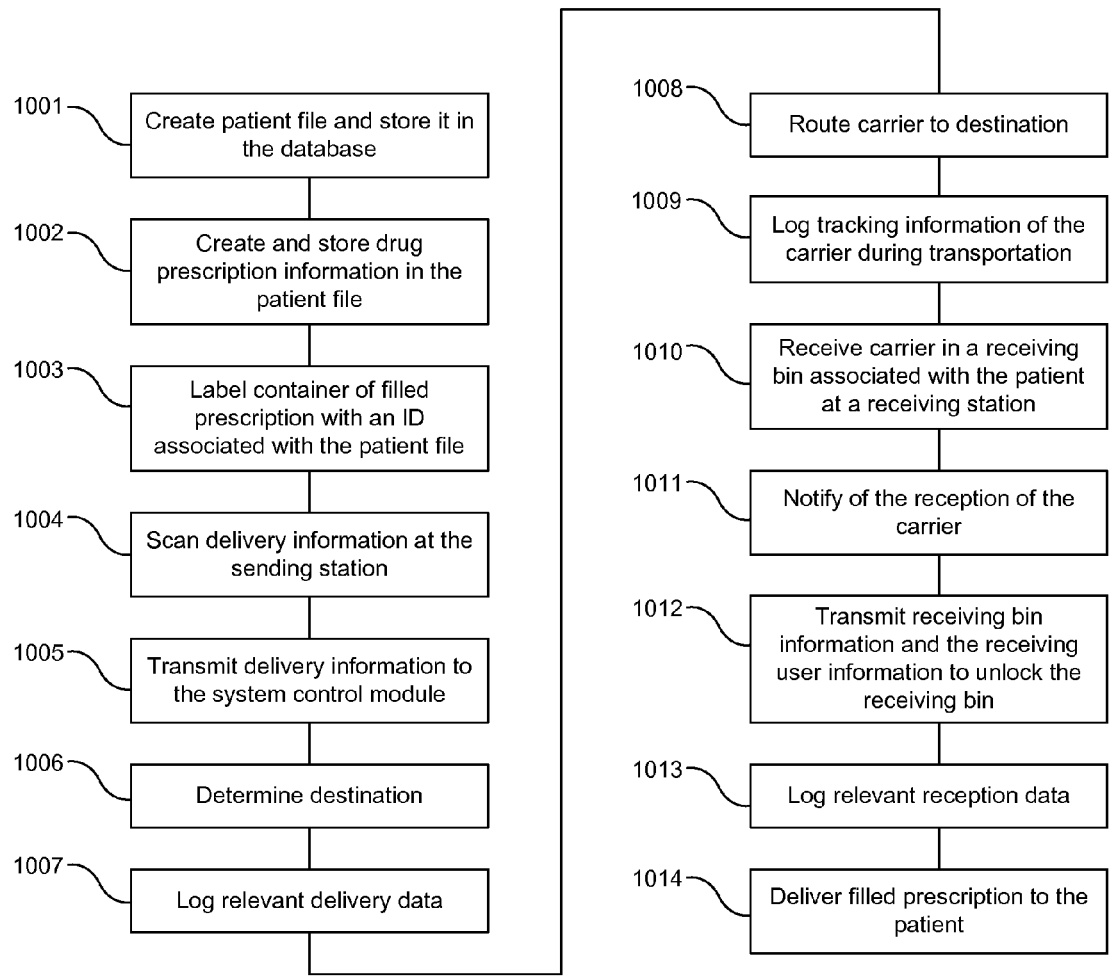
FIG. 10 is a flow chart illustrating a method for sending and receiving a carrier and payload from the sending station to a receiving station illustrated in FIG. 8 according to an embodiment of the present principles.

Referring now to FIG. 10 (as well as FIG. 8), a flowchart illustrating a method of sending carriers and payloads 810 from the sending station 824 to the receiving station 808 according to an embodiment of the present principles is shown. Initially, when a patient is admitted to the hospital, the hospital assigns the patient a patient ID and a receiving bin. Specifically, the hospital creates an electronic file of the patient that is stored in database 802 in step 1001. The file may include the patient ID, name of the patient, room number of the patient, bed number of the patient, receiving station ID associated with the patient, receiving bin ID associated with the patient, and IDs of authorized users allowed access to the receiving bin associated with the patient. The information may be dynamic and updated by the hospital staff as required. For example, the IDs of authorized users allowed access to the receiving bin may change from time to time depending on the changes of shifts of hospital personnel. Next, in step 1002, the doctor prescribes a drug, for example penicillin, to the patient and the patient file is updated with the drug information, for example, with the name, strength, and diluent of drug to be delivered to the patient. The prescription is sent to the pharmacy to be filled out. For example, the prescription may be electronically sent to the pharmacy via receiving station 808 by entering information through touch screen 829 or via a mobile communication device 834. Other system may also be utilized without departing from the scope of the present invention.

After the pharmacy fills out the prescription, the drug container is labeled in step 1003 with a unique ID tag which upon scanning retrieves the patient file. The drug container is then delivered to the sending station 824. To send a carrier from sending station 824, a user prepares contents of the carrier 810 for shipment. In step 1004, the sending user scans the delivery information, specifically the sending user ID, the ID tag 801 of the carrier 810, and the unique ID tag of the filled out prescription using tag reader 815. The sending user then inserts the filled out prescription into the carrier 810 and deposits the carrier 810 into the receiving bin 812 of the sending station 224. Tag reader 815 disposed at the sending station 824 sends the scanned information to the system control module 822 in step 1005. Using the unique ID tag of the filled out prescription, the system control module 822 accesses the patient file stored in database 802 and determines the physical destination of the carrier delivery in step 1006. Specifically, the system control module 822 retrieves the receiving bin ID associated with the patient. Relevant data received from the sending station 824 is logged in the database 802 in step 1007. This data may include the time the carrier was sent, the ID of the sending station 824, the sending user ID, and the ID tag 801 of the carrier.

The system control module 822 sends commands to the components of the pneumatic tube system 800 in step 1008 to route the carrier from the sending station 824 to a particular receiving bin 811 associated with the patient at the receiving station 808. As the carrier is transported within the pneumatic tube system 800, inline tag readers 820 scan the ID tag 801 of the carrier 810 and transmit that information to the system control module 822 to be logged as tracking information in database 802 in step 1009.

When the carrier arrives at the destined bin 811 of the receiving station 808 in step 1010, the carrier ID 810 is automatically scanned at the receiving station 808 to verify delivery, and the visual indicator 819 may light up to notify that a carrier has been received in step 1011. In addition, a notification may be send to a mobile communication device 834 of the receiving user that the prescription has been filled out and received by the receiving station 808. The receiving user may be a head nurse of the nursing station, or a doctor or nurse attending the patient. In step 1012, the receiving user unlocks the bin 811 associated with the patient at the receiving station 808 by transmitting selected bin information and the user identification information to the system control module 822. The receiving user may do so by scanning an ID tag 817 associated with the receiving bin with a mobile communication device 834 and entering the user identification information into the mobile communication device 834. The mobile communication device 834 transmits the information to the system control module 822, which looks up the patient file to determine whether the receiving user is authorized to access the receiving bin. If so, the system control module 822 sends a command to the receiving station 808 to unlock the receiving bin 811 associated with the patient. In step 1013, the system logs relevant reception data, including, for example, the carrier ID, the receiving station ID, the receiving bin ID, the time the carrier arrived at the receiving bin 811, the time the receiving bin has been unlocked, and the receiving user identification information. The contents of the carrier 810 are then delivered to the patient in step 1014. In that step, the mobile communication device 834 may be used to scan an ID tag on the patient's wristband or other ID tag located in the proximity of the patient, as well as the ID tag of the prescription to create a log that the prescription has been delivered to the patient. The patient may then receive an invoice directly for the filled prescription without hospital involvement.

It will be appreciated that although the above pneumatic tube carrier tracking system description is described as used in a hospital, the present principles are not limited to such use. For instance, the principles could be used in any other businesses or enterprises where customized product deliver is desired. While the foregoing embodiments of the principles have been set forth in considerable detail for the purposes of making a complete disclosure of the principles, it will be apparent to those of skill in the art that numerous changes may be made to such features without departing from the spirit and the scope of the present principles.

The invention claimed is:

1. A pneumatic tube carrier routing system comprising:
a receiving station comprising a plurality of receiving bins and no more than one dispatcher, wherein each receiving bin comprises a separate receiving area and a door preventing access to said separate receiving area of each receiving bin;
a sending station routably connected to the receiving station via pneumatic tubing, wherein the sending station comprises a carrier receiving bin and a tag reader that reads an identification tag of a carrier or of contents of a carrier to obtain destination information, wherein said destination information comprises identification of one receiving bin of the plurality of receiving bins of the receiving station;
a system control module in signal communication with the sending station and the receiving station, wherein the system control module comprises a database module that stores a list of users authorized to access said one receiving bin of the receiving station;
wherein the system control module receives the identification of the one receiving bin from the sending station and routes the carrier from the sending station to the one receiving bin of the receiving station through the pneumatic tubing;
wherein the system control module receives a selection of the one receiving bin and a user identification information from the receiving station or from a mobile device, verifies whether the user identification information matches a user from the list of users authorized to access said one receiving bin, and upon determining that the user identification information matches a user from the list of users authorized to access said one receiving bin, sends a command to the receiving station to unlock said door of the one receiving bin to allow the user to access the receiving bin.

2. The system according to claim 1, wherein each receiving bin of the receiving station comprises a presence sensor that detects presence of a carrier in the each receiving bin.

3. The system according to claim 1, wherein each receiving bin of the receiving station comprises a tag reader that reads an identification tag of a carrier for obtaining reception information.

4. The system according to claim 3, wherein the tag reader of each receiving bin of the receiving station reads tags consisting of at least one of an optically scannable identifier tag and a Radio Frequency Identification ("RFID") tag.

5. The system according to claim 1, wherein the tag reader of the sending station reads tags consisting of at least one of an optically scannable identifier tag and a Radio Frequency Identification ("RFID") tag.

6. The system according to claim 1, wherein the tag reader of the sending station captures information associated with at least one of a carrier contents ID, a carrier ID, a sending user ID, a sending station ID, and a receiving station ID.

7. The system according to claim 1, wherein each receiving bin of the receiving station comprises a visual indicator that visually indicates that a carrier has arrived at the each receiving bin.

8. The system according to claim 1, wherein notification is sent to the mobile device that indicates that the carrier has arrived at the one receiving bin of the receiving station.

9. The system according to claim 1, wherein notification is sent to the system control module that indicates that the carrier has arrived at the one receiving bin of the receiving station.

10. The system according to claim 1, wherein the receiving station comprises a touch screen that receives at least one of the selection of the one receiving bin and the user identification information.

11. The system according to claim 1, wherein the receiving station comprises a card reader that receives the user identification information.

12. The system according to claim 1, wherein the receiving station comprises a separate receiving bin that dispatches empty carriers back to the sending station.

13. The system according to claim 1 further comprising a diverter in direct communication with the receiving station, wherein the diverter comprises a plurality of outlet ports each in communication with a selected receiving bin of the plurality of receiving bins of the receiving station via pneumatic tubing.

14. The system according to claim 13, wherein the diverter is controlled by the system control module that instructs the diverter to divert the carrier to an outlet port in communication with the one receiving bin of the receiving station.

15. A method of automatically routing a pneumatic tube carrier from a sending station to one receiving bin of a receiving station, wherein the receiving station comprises a plurality of receiving bins and no more than one dispatcher, wherein each receiving bin comprises a separate receiving area and a door preventing access to said separate receiving area of each receiving bin, the method comprising:
  reading, via a tag reader associated with the sending station, an identification tag of a carrier or of contents of a carrier to obtain destination information, wherein said destination information comprises identification of the one receiving bin of the plurality of receiving bins of the receiving station;
  transmitting said identification of the one receiving bin from the receiving station to a system control module in signal communication with the sending station and the receiving station;
  storing a list of users authorized to access said one receiving bin of the receiving station in a database module associated with the system control module;
  receiving the carrier in a carrier receiving bin of the sending station;
  routing the carrier from the sending station to the one receiving bin of the receiving station through pneumatic tubing;
  receiving a selection of the one receiving bin of the receiving station and a user identification information from the receiving station or from a mobile device;
  verifying whether the user identification information matches a user from the list of users authorized to access said one receiving bin; and
  upon determining that the user identification information matches a user from the list of users authorized to access said one receiving bin, sending a command to the receiving station to unlock said door of the one receiving bin, allowing the user to access the receiving bin.

16. The method according to claim 15, further comprising: detecting presence of the carrier in the one receiving bin of the receiving station via a presence sensor.

17. The method according to claim 15, further comprising: reading the identification tag of the carrier via a tag reader of the one receiving bin of the receiving station to receive reception information.

18. The method according to claim 15, wherein the tag reader of the sending station reads tags consisting of at least one of an optically scannable identifier tag and a Radio Frequency Identification ("RFID") tag.

19. The method according to claim 15, wherein the tag reader of the sending station captures information associated with at least one of a carrier contents ID, a carrier ID, a sending user ID, a sending station ID, and a receiving station ID.

20. The method according to claim 15, further comprising: visually indicating that the carrier has arrived at the one receiving bin of the receiving station via a visual indicator.

21. The method according to claim 15, further comprising: receiving at least one of the selection of the one receiving bin and the user identification information via a touch screen of the receiving station.

22. The method according to claim 15, further comprising: receiving user identification information via a card reader of the receiving station.

* * * * *